(12) United States Patent
Riggall

(10) Patent No.: US 7,025,709 B2
(45) Date of Patent: Apr. 11, 2006

(54) THERAPEUTIC GLOVE APPARATUS

(76) Inventor: Cynthia A. Riggall, 2724 Night Hawk Ct., Longwood, FL (US) 32779

( * ) Notice: Subject to any disclaimer, the term of this patent is extended or adjusted under 35 U.S.C. 154(b) by 529 days.

(21) Appl. No.: 10/051,688

(22) Filed: Jan. 22, 2002

(65) Prior Publication Data

US 2003/0139258 A1  Jul. 24, 2003

(51) Int. Cl.
*A63B 23/14* (2006.01)
*A63B 23/16* (2006.01)
*A41D 19/00* (2006.01)

(52) U.S. Cl. ............................ 482/49; 482/44; 2/160

(58) Field of Classification Search ............ 482/44–50; 602/20–21, 64; 128/878–879, 882; 2/16, 2/159–160
See application file for complete search history.

(56) References Cited

U.S. PATENT DOCUMENTS

| 3,741,207 A |   | 6/1973  | Fuson |           |
|-------------|---|---------|-------|-----------|
| 4,173,218 A |   | 11/1979 | Cronin |          |
| 4,706,658 A |   | 11/1987 | Cronin |          |
| 4,945,571 A |   | 8/1990  | Calvert |         |
| 5,070,223 A | * | 12/1991 | Colasante | 219/759 |
| 5,218,719 A | * | 6/1993  | Johnson | 2/19   |
| 5,259,369 A |   | 11/1993 | Matsumura et al. |  |
| 5,297,541 A |   | 3/1994  | Hensey |          |
| 5,333,605 A |   | 8/1994  | Matsumura et al. |  |
| 5,345,609 A | * | 9/1994  | Fabry et al. | 2/20 |
| 5,537,688 A |   | 7/1996  | Reynolds et al. | |
| 5,557,803 A | * | 9/1996  | Granich et al. | 2/16 |
| 6,093,165 A | * | 7/2000  | Estwanik | 602/64 |
| 6,141,801 A | * | 11/2000 | Helenick | 2/159 |
| 6,430,751 B1 | * | 8/2002 | Tourbier et al. | 2/160 |

* cited by examiner

*Primary Examiner*—Stephen K. Cronin
*Assistant Examiner*—Fenn C. Mathew
(74) *Attorney, Agent, or Firm*—William M. Hobby, III

(57) ABSTRACT

A therapeutic glove apparatus has a first glove half formed of a flexible material and shaped to cover one side of a person's hand and has a bladder broken into cells and filled with a viscous liquid, such as a fluid clay material. A second glove half is formed of a flexible material and shaped to cover the other side of a person's hand and is movably attached to the first glove half and also has a bladder having a plurality of cells formed therein filled with a viscous material, such as a fluid clay. Attaching straps have hook and loop material thereon for attaching the first and second glove halves for removably attaching a therapeutic glove over a person's hand. The therapeutic glove allows a person to exercise the muscles of the hands, fingers, and wrists by movement against the resistance of clay while applying heat or cold to a person's hand.

2 Claims, 2 Drawing Sheets

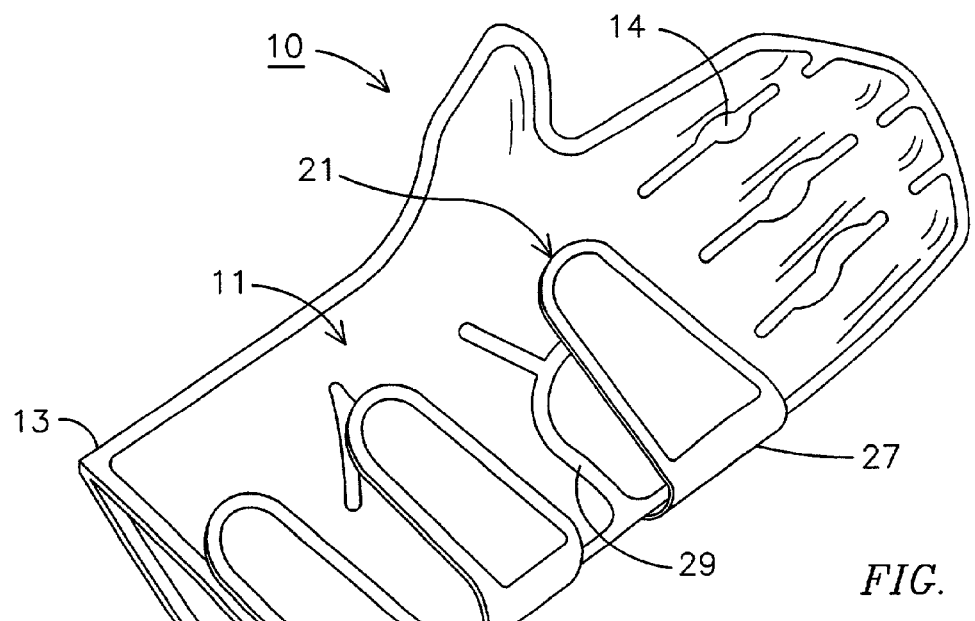
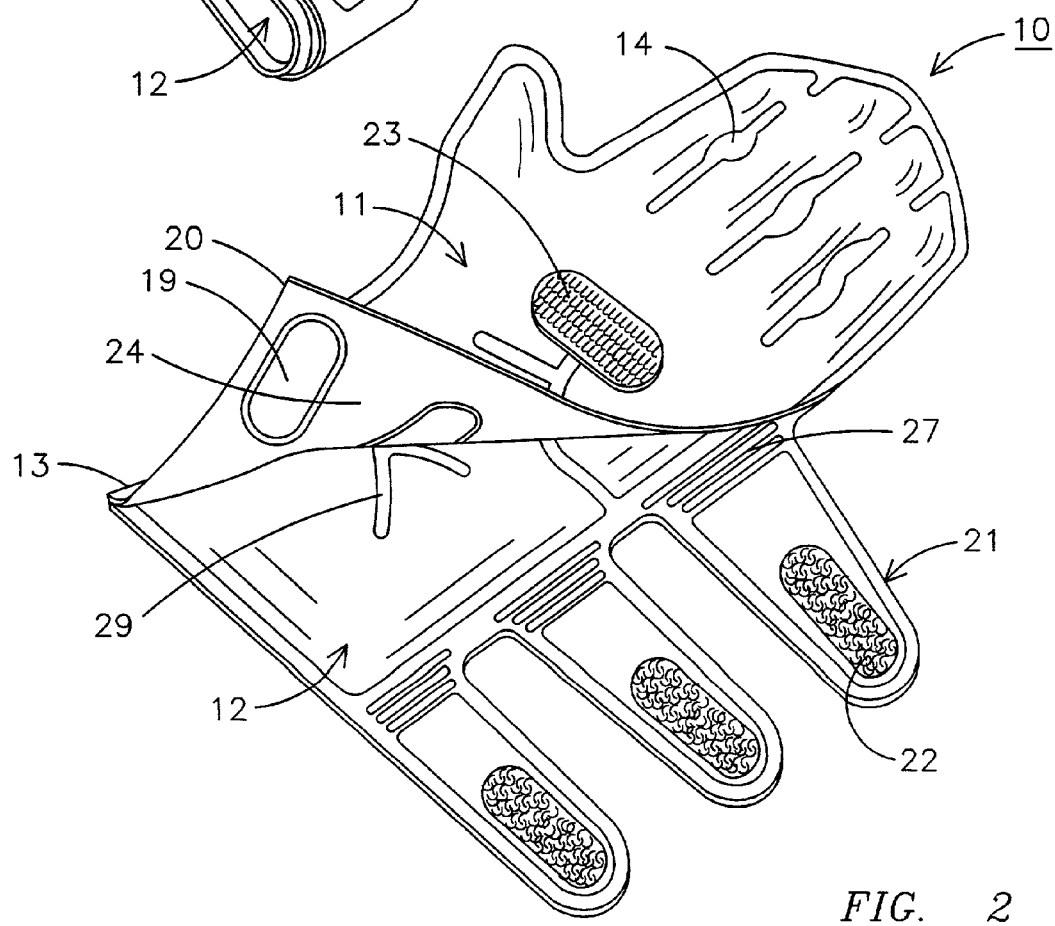
FIG. 1
FIG. 2

THERAPEUTIC GLOVE APPARATUS

BACKGROUND OF THE INVENTION

The present invention relates to a therapeutic glove and especially to a therapeutic glove for the application of heat or cold to a person's hand while exercising the hand.

A variety of therapeutic hand and exercising devices have been provided in the past as well as various devices for heating and cooling a person's hand. Prior patents which provide therapeutic gloves or the like include the Hensey U.S. Pat. No. 5,297,541 for an athletic therapeutic glove for exercising the muscles of the fingers, hands, and wrists and forearms. It is fabricated from a flexible material and has a plurality of elongated tube-shaped elastomeric bladders which are pressurized with air. The Matsumura et al. U.S. Pat. No. 5,259,369 is a remedial device for hand insufficiency and has a plurality of air sacks inflatable with compressed air. The Cronin U.S. Pat. No. 4,173,218 is a glove splint for an arthritic hand and has a glove-like envelope filled with a fluid for encapsulating the hand, thumb and fingers to provide a shock absorbing buffer to the hand. The Cronin U.S. Pat. No. 4,706,658 is a glove splint which has a glove-like envelope which is filled with fluid to encapsulate the hand. The Matsumura et al. U.S. Pat. No. 5,333,605 is a remedial device for hand insufficiency which uses compressed air inflating air sacks in the first and second bag bodies covering the hand. The Reynolds et al. U.S. Pat. No. 5,537,688 is a hand covering with vibration reducing bladder and includes a plurality of cells forming a bladder which are filled with air or a compressible fluid. The Fuson U.S. Pat. No. 3,741,207 is a hand restraining mitt which includes a chamber either inflated with air or filled with a resilient block of foam-like material to conform to the natural curvature of the wearer's hand.

The present invention advantageously includes a therapeutic glove having a plurality of bladders formed therein and filled with a viscous material, such as a fluid clay material, which advantageously can be heated or cooled for applying heat therapy to the hand while providing an exercise medium for bending and squeezing the clay filled glove.

SUMMARY OF THE INVENTION

A therapeutic glove apparatus has a first glove half formed of a flexible material and shaped to cover one side of a person's hand and has a bladder broken into cells and filled with a viscous liquid, such as a fluid clay material. A second glove half is formed of a flexible material and shaped to cover the other side of a person's hand and is movably attached to the first glove half and also has a bladder having a plurality of cells formed therein filled with a viscous material, such as a fluid clay. Attaching straps have hook and loop material thereon for attaching the first and second glove halves for removably attaching a therapeutic glove over a person's hand. The therapeutic glove allows a person to exercise the muscles of the hands, fingers, and wrists by movement against the resistance of clay while applying heat or cold to a person's hand.

BRIEF DESCRIPTION OF THE DRAWINGS

Other objects, features, and advantages of the present invention will be apparent from the written description and the drawings in which:

FIG. 1 is a perspective view of a therapeutic glove in accordance with the present invention;

FIG. 2 is a perspective view of the therapeutic glove of FIG. 1 partially opened for placement on a person's hand;

DESCRIPTION OF THE PREFERRED EMBODIMENT

Figure 3:
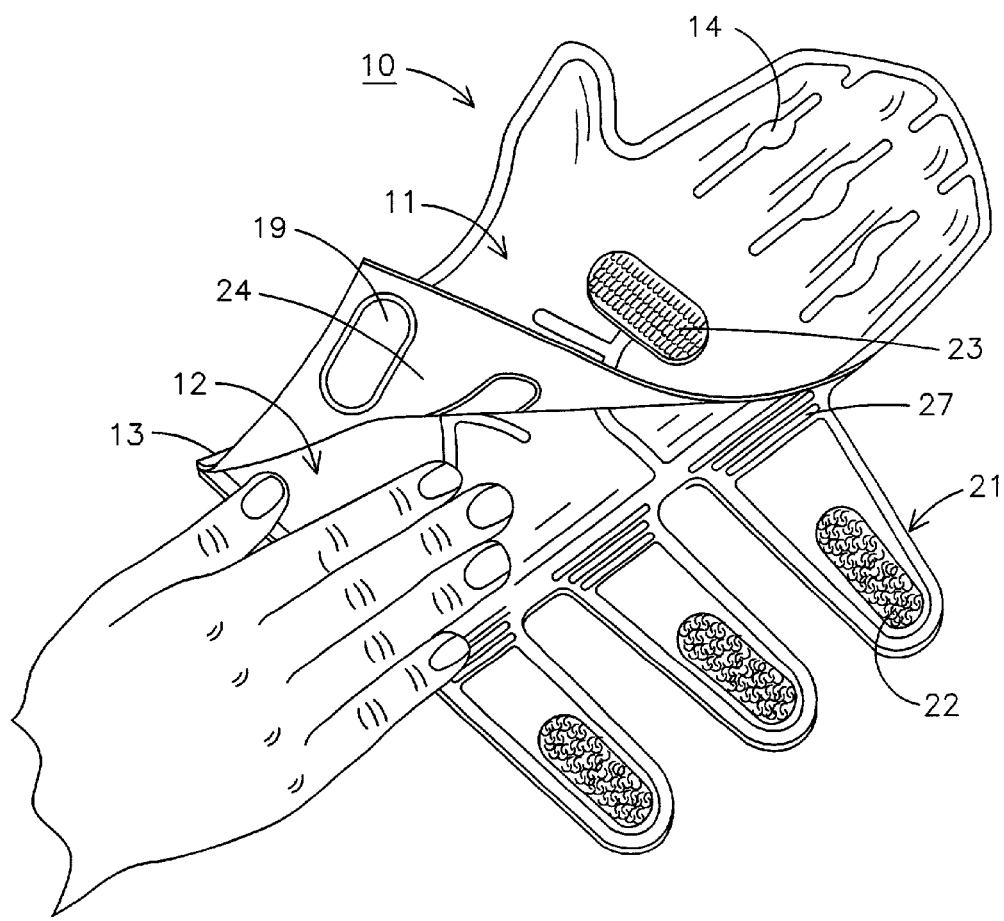
FIG. 3 is a perspective view of the therapeutic glove of FIGS. 1 and 2 having a person's hand being inserted.
Figure 4:
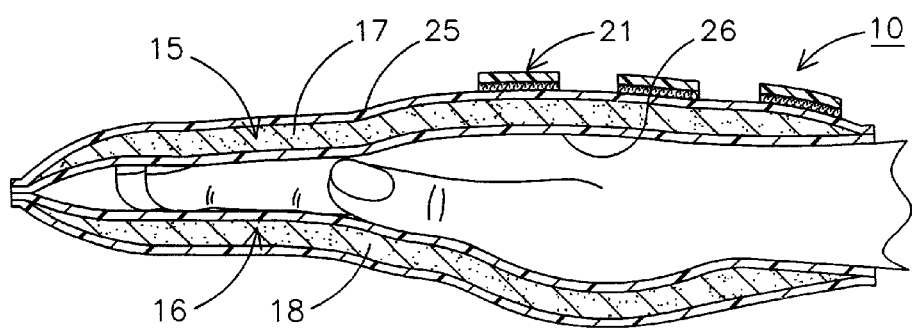
FIG. 4 is a sectional view taken through the therapeutic glove of FIGS. 1–3 having a person's hand therein.

Referring to the drawings of FIGS. 1–4, a therapeutic glove 10 is illustrated having a top glove half 11 and a bottom glove half 12 which glove halves are connected with a flexible hinge 13. The upper half 11 and the bottom half 12 are bound together with heat welding or the like at strips or voids 14 to form fingers for the glove but also to break up the internal bladder 15 of the upper half 11 and the internal bladder 16 of the bottom glove half 12. The breaking up of the internal bladder 15 and 16 into cells with buffers also impairs the flow and accumulation of viscous fluid 17 in the bladder 15 and the viscous fluid 18 in the bladder 16 by providing resistance to the movement of the fluid in the glove. The glove portion 20 as seen in FIG. 2 can be raised for sliding the hand in, as seen in FIG. 3. Once the hand is slid in, as shown in FIG. 4, a plurality of attaching straps 21 each having a piece of hook and loop material 22 thereon, are attached together. The glove top half 11 has a piece of hook and loop material 23 for attaching to each piece of hook and loop material 22. Each strap 21 hook and loop material 22 is aligned with one piece of hook and loop material 23 so that the bottom glove half 12 can be strapped to the top glove half 11, as shown in FIG. 1, and then adjusted for a particular person's hand. The glove also has a plurality of buffer portions or cells 24 separated by void areas 19 and 29 which are formed by welding portions of the flexible material 25 to the flexible bottom material 26 of the upper glove half 11. Similar cell shapes can be formed in the bottom glove half 12. Each of the straps 21 has a flexible hinge 27 binding it to the glove bottom half 12 so that the glove can be easily formed of flexible materials forming upper glove half and bottom glove half bladders which are broken into bladder sections and which can be permanently filled with the viscous material 17 and 18, as shown in FIG. 4. This material is permanently sealed within the bladder portion and may be a fluid clay, such as clay having water or other liquid in it to make it moveable. This advantageously allows the glove to be heated or cooled prior to placing on a person's hand for the therapeutic value of the heat and also allows for exercising the hand by the movement of the fingers, wrist, and hand. Movement of the hand exercises the muscles of the fingers, hand and wrist by the squeezing of the clay, such as the commercially available hand exercising devices shaped like balls with flexible exteriors and having a heavy viscous material thereinside.

It should be clear at this time that a therapeutic glove apparatus has been provided. However, the present invention should not be construed as limited to the forms shown which should be considered illustrative rather than restrictive.

I claim:

1. A therapeutic glove comprising:
    a first glove half formed of a flexible material and shaped to cover one side of a person's hand, said first glove half having a plurality of cells formed therein filled with viscous clay material;

a second glove half formed of a flexible material and shaped to cover the other side of a person's hand and being movably attached to said first glove half, said second glove half having a plurality of cells formed therein filled with a viscous clay material; and attaching means attached to said first glove half and to said second glove half for removably attaching said first glove half to said second glove half over a person's hand;

whereby a therapeutic glove allows a person to exercise the muscles of the hand, fingers, and wrist during the application of heat or cold to the person's hand.

2. A therapeutic glove in accordance with claim 1 in which said attaching means includes hook and loop material attached to said first and second glove halves.

* * * * *